United States Patent [19]
Merle et al.

[11] Patent Number: 5,703,643
[45] Date of Patent: Dec. 30, 1997

[54] SIGHT-TRACKING VIEWING DEVICE

[75] Inventors: Jean-Pierre Merle, Orsay; Martine Lassalle, Voisins le Bretonneux; Franck Bernoux, L'Hay-les-Roses; Maurice Adda, Antony, all of France

[73] Assignee: Aerospatiale Société Nationale Industrielle, Paris, France

[21] Appl. No.: 421,561

[22] Filed: Apr. 13, 1995

[30] Foreign Application Priority Data

Apr. 18, 1994 [FR] France ................... 94 04587

[51] Int. Cl.⁶ .......................................... H04N 5/225
[52] U.S. Cl. ............................... 348/341; 396/51
[58] Field of Search .......................... 348/333, 341, 348/334, 335; 351/221, 211, 205, 206; 354/219; 396/51, 373, 384

[56] References Cited

U.S. PATENT DOCUMENTS

| | | | |
|---|---|---|---|
| 5,311,225 | 5/1994 | Acier et al. | 351/221 |
| 5,321,456 | 6/1994 | Yoon | 354/219 |

FOREIGN PATENT DOCUMENTS

| | | |
|---|---|---|
| 0042812 | 12/1981 | European Pat. Off. |
| 0157973 | 10/1985 | European Pat. Off. |
| 2685099 | 6/1993 | France |
| 900021 | 7/1949 | Germany |
| 1219250 | 6/1966 | Germany |
| 2322017 | 11/1974 | Germany |
| 3639869 | 3/1988 | Germany |
| 0217880 | 9/1988 | Japan |

OTHER PUBLICATIONS

Journal Of The Optical Society of America, vol. 48, No. 7, Jul. 1958, pp. 439–445.

Primary Examiner—Andrew Faile
Assistant Examiner—Christopher Onuaku
Attorney, Agent, or Firm—Marshall, O'Toole, Gerstein, Murray & Borun

[57] ABSTRACT

A device intended to be associated, on the one hand, with a viewfinder, on the eyepiece side thereof, and, on the other hand, with a calculating mechanism, to form a system making it possible to determine at every instant that portion of a field sighted by the eye of an observer through the viewfinder. The device is arranged on the image side of the eyepiece of the viewfinder and includes a splitter element associated with a thick optical plate whose parallel faces are orthogonal to the optical axis of the finder.

8 Claims, 2 Drawing Sheets

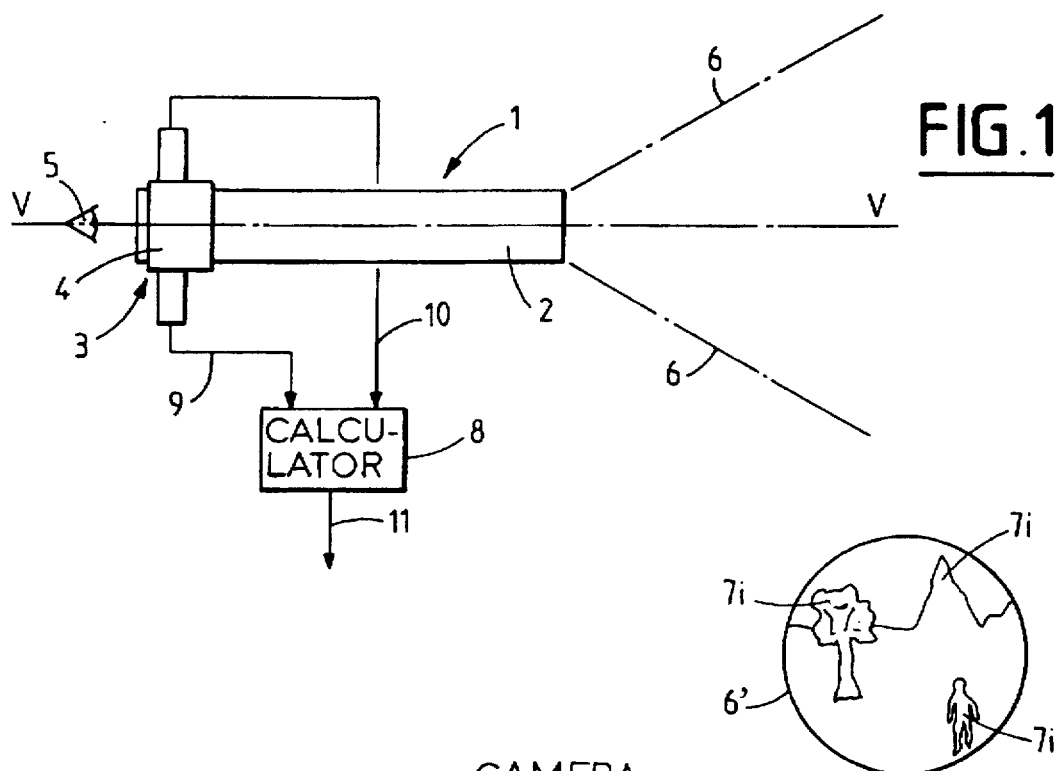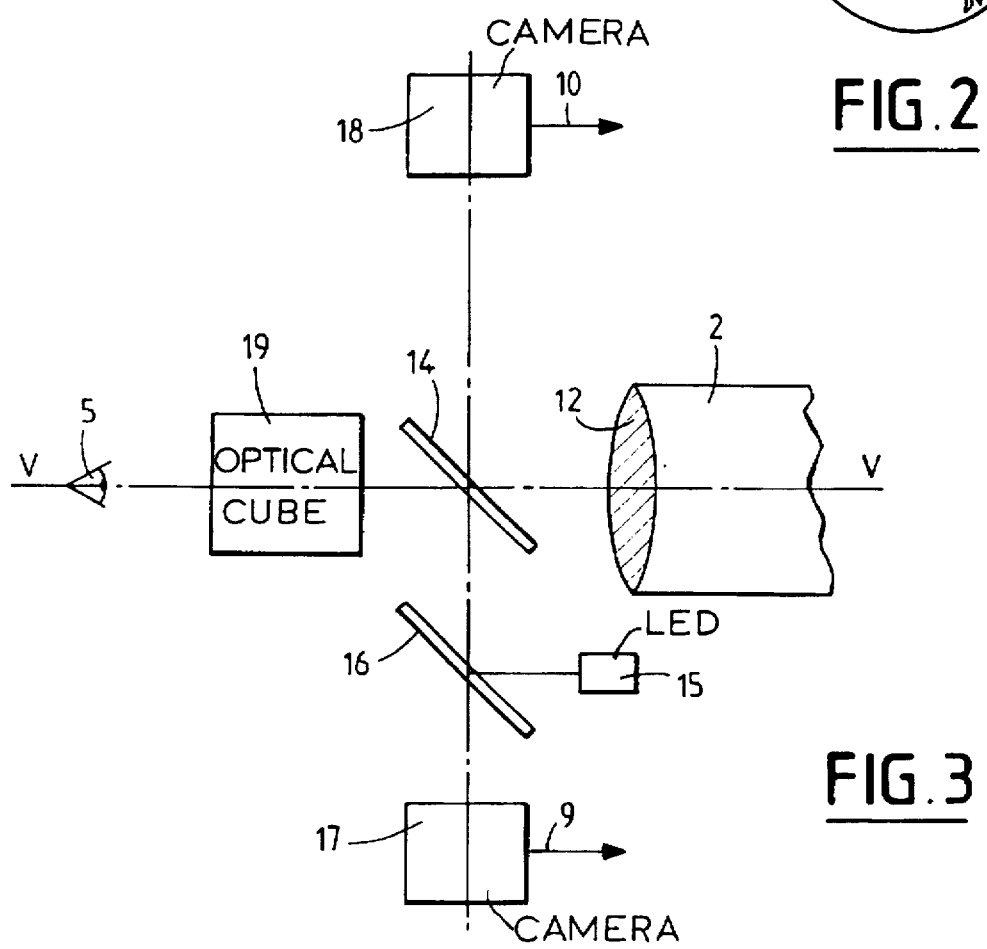

SIGHT-TRACKING VIEWING DEVICE

BACKGROUND OF THE INVENTION

The present invention relates to a device intended to be associated, on the one hand, with a viewfinder, on the eyepiece side thereof, and, on the other hand with calculating means, to form a system making it possible to determine at every instant that portion of a field sighted by the eye of an observer through said viewfinder.

A system is already known, for example through the patent EP-A-0 157 973, which is intended to determine that portion of a field sighted by the eye of an observer and comprising:

- a light source sending a light beam to the cornea of said eye in order to form a corneal reflection; first picture-taking means observing said corneal reflection and generating first electrical signals representative of the orientation of the optical axis of said eye;
- second picture-taking means observing said field and generating second electrical signals representative of said field; and
- calculating means receiving said first and second electrical signals and determining, within said field, the portion of the latter sighted by said eye.

The operation of such a device is based in particular on the teachings contained in the publication by MACKWORTH et al., "Eye Fixations Recorded on Changing Visual Scenes by the Television Eye Marker" in Journal of the Optical Society of America, July 1958, and showing that there is a correlation between the variation in the orientation of the optical axis of the eye and the displacement of said corneal reflection.

Consequently, by observing said corneal reflection, said first picture-taking means know, at every instant, the position of the corneal reflection and hence the orientation of the optical axis of the eye. Said calculating means can therefore determine that portion of the field sighted, at every instant, by said eye, because they receive the field information originating from the second picture-taking means.

Said first and second picture-taking means can be of the camera type, for example of the CCD type and, preferably, said light source is invisible (infrared) so as not to bother the observer. It is generally of the LED diode type.

According to a known variant implementation, the retinal reflection generated by said light beam and stopped down by the pupil can be associated with said corneal reflection, so as to determine the orientation of the optical axis of the eye.

In most of the known devices, of the type described above, headgear or glasses are provided, which are worn by said observer and carry at least some of the constituent elements (light source, cameras, . . . ) of the device. This results in obvious bother and discomfort to the observer.

Moreover, in these known devices with headgear or glasses, the eye of the observer is able to look only directly at the field, without interposition of an optical system, such as a viewfinder, limiting peripheral vision. There is therefore no obstacle to the illumination of the eye by the invisible light source.

On the other hand, when wishing to provide an optical system for observation of the field by the eye of the observer, difficulties are encountered.

In fact, the eye has to be close to the eyepiece of the optical system, in the plane of the pupil of said optical system. Consequently, it is not possible, lacking space, to introduce the invisible light beam between the eyepiece of the optical system and the eye. Furthermore, the conception of illuminating the eye with invisible light through said optical system would limit the diameter of the beam of invisible light by the pupil of said optical system. Given that the area of the pupil of an optical system is small compared with the area of the cornea to be illuminated, it would be impossible to illuminate the entire cornea and hence measure all the orientations of the optical axis of the eye.

To overcome the latter drawbacks, the document FR-A-2 685 099 (91 15509) provides, in connection with FIG. 4 thereof, a device placed inside said optical system, in the vicinity of the object focus of its exit eyepiece, this device comprising:

- an optical splitter element arranged on the optical axis of said viewfinder;
- a light source sending a light beam to said eye, by way of said optical splitter element, in order to form a reflection;
- first picture-taking means observing said reflection by way of said optical splitter element and generating first electrical signals representative of the orientation of the optical axis of said eye, said first signals being required to be sent to the calculating means; and
- second picture-taking means observing said field by way of said optical splitter element and generating second electrical signals representative of said field, said second signals likewise being required to be sent to said calculating means.

Such a device, although it resolves the aforesaid drawbacks, nevertheless has that of requiring it to be arranged inside the viewfinder, thus heightening the difficulties of emplacement, fitting and adjustment.

SUMMARY OF THE INVENTION

The purpose of the present invention is to overcome these drawbacks.

To this end, according to the invention, the device of the type described above is notable in that it is arranged on the image side of the eyepiece of said viewfinder (that is to say outside the latter) and in that it moreover includes a thick optical plate whose parallel faces are orthogonal to said optical axis of said finder.

Thus, by virtue of said thick optical plate, the exit pupil of the viewfinder is distanced from the eyepiece of the latter and sufficient space is created downstream of the eyepiece of the finder to accommodate said device between the eye-and said eyepiece. Said thick optical plate can be arranged between said optical splitter element and the eye, or else between the eyepiece of the viewfinder and said optical splitter element.

So that the distancing of the exit pupil is sufficient without requiring too large a thickness for the parallel-face plate, it is advantageous for the refractive index of the latter to be high, for example around 2.

It will be noted that the document FR-A-2 685 099 mentioned above provides in connection with FIG. 3 thereof for the placement, outside the viewfinder, of a device different to that described in connection with FIG. 4. However, then, an afocal optical vehicle is provided, consisting of a plurality of lenses. Such an optical vehicle is complex and the source of stray reflections bouncing back by reflection from lens to lens, and capable of disturbing the proper operation of the device. On the other hand, by virtue of the thick plate according to the invention, a simple device is obtained free of adjustment and devoid of stray reflections.

In an advantageous embodiment, said thick optical plate has the shape at least approximately of a cube.

Said optical splitter element can be of the thin parallel plate with treated surfaces type so as to be, on one side, partially transparent and partially reflecting in respect of the light rays originating from said field and, on the other side, at least partially reflecting in respect of said light beam emitted by said light source.

In order to save even more space downstream of the eyepiece of the viewfinder, it is then advantageous for said optical splitter element to be incorporated into said cube, along a diagonal plane thereof.

Preferably, said device forms a construction unit which can be removably attached to said viewfinder.

It will be noted that such an embodiment is particularly advantageous since it makes it possible to adapt said viewfinder, without modifying the latter, in order to use it with the device according to the present invention. A device is thus obtained which is intended to be coupled with a regular viewfinder so as to make the latter suitable for viewing together with sight-tracking.

However, it goes without saying that the device according to the invention could be incorporated in the viewfinder, downstream of the eyepiece. Even in this case, there would be no internal modification of the viewfinder.

In an advantageous embodiment, the device of the invention includes a mount securing together the cube provided with the splitter element and the first and second picture-taking means, and also means for fixing said mount onto said viewfinder.

The figures of the appended drawing will elucidate the manner in which the invention can be embodied. In these figures, identical references denote similar elements.

BRIEF DESCRIPTION OF THE DRAWINGS

FIG. 1 shows diagrammatically an embodiment of the device according to the present invention.

FIG. 2 shows diagrammatically the image of a field viewed through the device of the invention.

FIG. 3 is a view illustrating the makeup of a first exemplary embodiment of the device of FIG. 1.

DETAILED DESCRIPTION OF A PREFERRED EMBODIMENT

Figure 5:
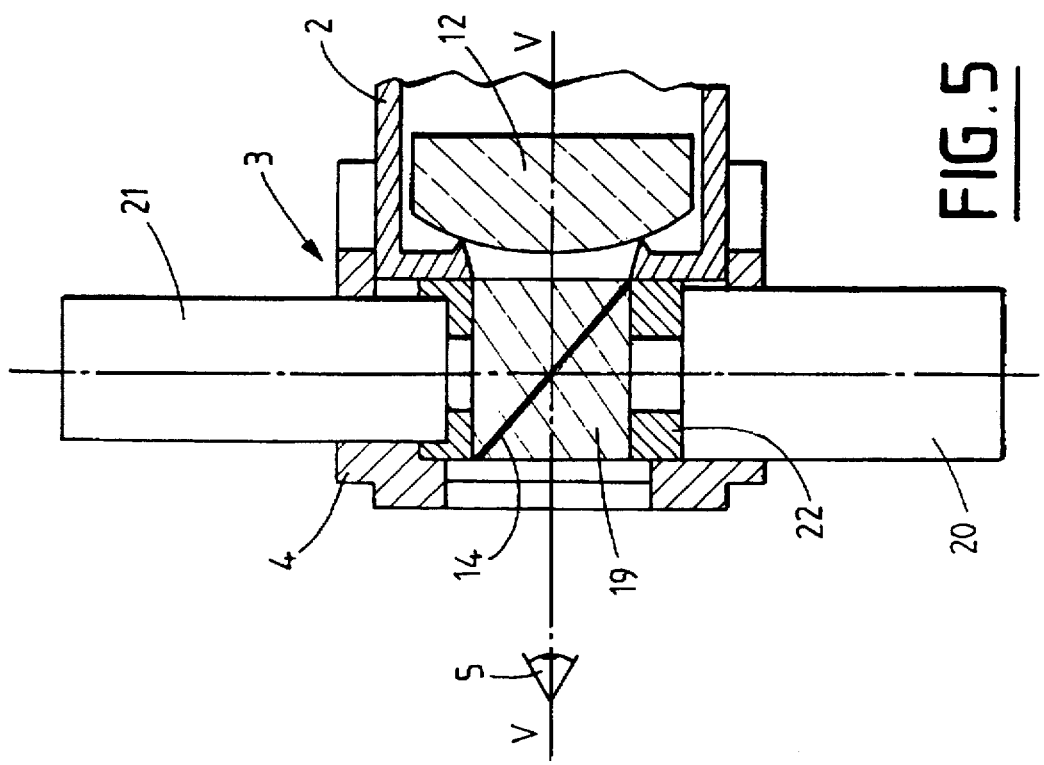
FIG. 5 illustrates in partial section a practical embodiment of the second example of the device according to the present invention.

The system 1, according to the present invention and represented diagrammtically in FIG. 1, includes a viewfinder 2, for example of the astronomical finder type, and an optical-electrical device 3, which are secured to one another on the eyepiece side of said finder by a fixing element 4, so that their optical axes are strictly aligned with a common optical axis defining a viewing line V—V.

An eye 5 of an observer is arranged on the viewing line V—V, behind the device 3, so that it can sight the field 6 defined by the viewfinder 2. As illustrated in FIG. 2, the eye 5 therefore views the image 6' of the field 6 through the finder 2 and the device 3, as well as the images of the various elements or portions 7i making up this field.

Furthermore, the system 1 of FIG. 1 includes a calculator 8 receiving electrical signals from outputs 9 and 10 of the device 3 and processing them so as to deliver signals at its output 11.

In the diagrammatic FIG. 3, the finder is represented only partially.

The finder 2 includes an eyepiece 12 and the eye 5 is arranged behind this eyepiece so as to receive the optical beam passing through said finder (originating from the objective, not represented, of the said finder 2) and so as to view the image 6' (FIG. 2) of the field 6.

Between the eye 5 and the eyepiece 12 is arranged an inclined plate 14 which, on one side, is partially transparent and partially reflecting in respect of the optical beam passing through the finder, and, on the other side, at least partially reflecting in respect of the infrared light.

Moreover, the device of FIG. 3 includes:

an infrared light source 15 (LED diode), emitting an infrared beam, which, through the action of a semi-transparent inclined mirror 16, is directed onto the inclined plate 14;

an infrared CCD camera 17 arranged facing the inclined plate 14, the output of the camera 17 forming the output 9 of the finder 2;

a CCD camera arranged facing the inclined plate 14, the output of the camera 18 forming the output 10 of the finder 2; and an optical cube 19, of high refractive index (around 2), arranged on the viewing line V—V with two of its opposite faces orthogonal to said viewing line. Said optical cube 19 can be placed between the eye 5 and the inclined plate 14 (as represented in FIG. 3), but it can also be arranged between said inclined plate 14 and the eyepiece 12.

Thus, the optical beam passing through the viewfinder 2 is sent to the eye 5 through the eyepiece 12, the inclined plate 14 and the cube 19. Moreover, part of said optical beam is sent to the camera 18 by reflection off the inclined plate 14. The electrical signals appearing at the output 10 therefore represent the image 6' of the field 6.

The infrared beam emitted by the source 15 is sent to the eye 5 after reflection off the semitransparent mirror 16 and off the inclined plate 14, followed by passage through the cube 19. This infrared beam therefore generates, by illuminating the cornea, the retina and/or the pupil of the eye 5 and by reflection off them, a corneal, retinal and/or pupillary reflection conveyed by a reflected infrared beam which passes through the cube 19, in the reverse direction to the infrared illuminating beam, is reflected off the inclined plate 14 and passes through the semitransparent mirror 16, before being sent to the camera 17. The electrical signals appearing at the output 9 therefore represent the corneal and/or retinal reflection.

Consequently, the calculator 8 receiving at its inputs the electrical signals originating from the outputs 9 and 10 of the cameras 17 and 18 is capable of delivering at its output 11, through known processing of said electrical input signals, electrical output signals representative of said element 7i sighted by the eye 5.

From the above description it will be noted that it is easy to embody, by virtue of the invention, a dual-eyepiece device by associating an optical system 2, 3 with each of the two eyes 5 of an observer. In this case, it is advantageous for the calculator 8 to process the signals originating from the two optical systems 2, 3.

Figure 4:
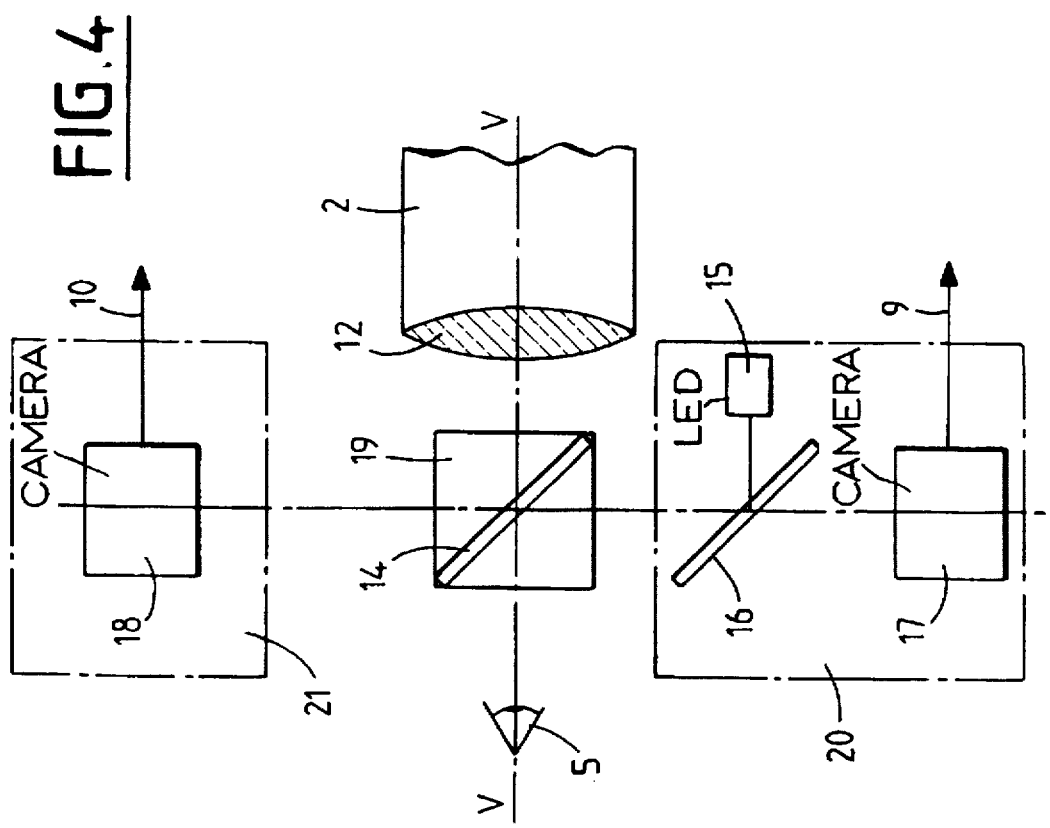
FIG. 4 is a view illustrating the makeup of a second exemplary embodiment of the device of FIG. 1.

The various elements 14 to 19 of FIG. 3 are found again in the exemplary embodiment of FIG. 4. However, in this case, the inclined plate 14 is incorporated into the optical cube 19, along a diagonal plane thereof.

As FIG. 5 shows, in a practical embodiment of the example of FIG. 4, there is provided:

a box 20 housing the camera 17, the infrared source 15 and the semitransparent mirror 16;

a box 21 housing the camera 18;

a mount 22 securing the cube 19 (together with the plate 14) and the boxes 20 and 21 so as to form the device 3; and a fixing device 4 making it possible to secure the device 3 to the viewfinder 2, on the image (or exterior) side of the eyepiece 12.

Of course, the fixing device 4 can be removable or permanent.

We claim:

1. A device for use with a viewfinder, on the eyepiece side thereof, and, with a calculating means, to form a system to determine at every instant that portion of a field sighted by the eye of an observer through said viewfinder, said device comprising:

an optical splitter element arranged on the optical axis of said viewfinder;

a light source sending a light beam to said eye, by way of said optical splitter element, in order to form a reflection;

first picture-taking means observing said reflection by way of said optical splitter element and generating first electrical signals representative of the orientation of the optical axis of said eye, said first signals being required to be sent to said calculating means; and second picture-taking means observing said field by way of said optical splitter element and generating second electrical signals representative of said field, said second signals likewise being required to be sent to said calculating means, wherein said device is arranged on the image side of the eyepiece of said viewfinder and includes a thick optical plate whose parallel faces are orthogonal to said optical axis of said finder, said thick optical plate having a shape at least approximately of a cube.

2. The device as claimed in claim 1, wherein the refractive index of said thick optical plate is approximately 2.

3. The device as claimed in claim 1, wherein said optical splitter element is a thin plate with treated surfaces.

4. The device as claimed in claim 3, wherein said optical splitter element is, on one side, partially transparent and partially reflecting in respect of the light rays originating from said field and, on the other side, at least partially reflecting in respect of said light beam emitted by said light source.

5. The device as claimed in claim 1, wherein said optical splitter element is incorporated into said cube, along a diagonal plane thereof.

6. The device as claimed in claim 5, wherein the device includes a mount securing together the cube provided with the splitter element and the first and second picture-taking means, and means for fixing said mount to said viewfinder.

7. The device as claimed in claim 1, wherein the device forms a construction unit which can be removably attached to said viewfinder.

8. The device as claimed in claim 1, wherein the device solidly secured to said viewfinder.

* * * * *